(12) United States Patent
Gray et al.

(10) Patent No.: US 7,282,524 B2
(45) Date of Patent: Oct. 16, 2007

(54) ALKANOLAMIDE SURFACTANT EMULSIONS AND PROCESS THEREFOR

(75) Inventors: John Gray, Round Rock, TX (US); Eugene D'Aversa, Blue Island, IL (US)

(73) Assignee: McIntyre Group, Ltd., University Park, IL (US)

( * ) Notice: Subject to any disclaimer, the term of this patent is extended or adjusted under 35 U.S.C. 154(b) by 475 days.

(21) Appl. No.: 10/892,750

(22) Filed: Jul. 16, 2004

(65) Prior Publication Data

US 2004/0266891 A1 Dec. 30, 2004

Related U.S. Application Data

(63) Continuation of application No. 09/937,592, filed as application No. PCT/US00/09927 on Apr. 14, 2000, now Pat. No. 6,765,024.

(60) Provisional application No. 60/287,574, filed on Apr. 14, 1999.

(51) Int. Cl.
| | |
|---|---|
| B01F 3/08 | (2006.01) |
| A61K 8/04 | (2006.01) |
| C11D 1/90 | (2006.01) |
| C11D 1/94 | (2006.01) |
| C11D 1/88 | (2006.01) |

(52) U.S. Cl. ............ 516/67; 516/69; 516/926; 510/416; 510/417; 510/502; 510/125; 510/126; 510/135; 510/138; 510/237; 510/123

(58) Field of Classification Search ............. 516/67, 516/69, 926; 510/123, 416, 417, 502, 125, 510/126, 135, 138, 237

See application file for complete search history.

(56) References Cited

U.S. PATENT DOCUMENTS

| | | | |
|---|---|---|---|
| 4,154,706 A | 5/1979 | Kenkare et al. | |
| 4,243,549 A | 1/1981 | Messenger et al. | |
| 4,312,771 A | 1/1982 | Matsuda | |
| 4,440,665 A | 4/1984 | Mather et al. | |
| 4,620,976 A | 11/1986 | Quack et al. | |
| 4,654,163 A | 3/1987 | Quack et al. | |
| 4,668,422 A | 5/1987 | Malik et al. | |
| 4,692,271 A | 9/1987 | Messenger et al. | |
| 4,753,754 A | 6/1988 | Messenger et al. | |
| 4,824,594 A * | 4/1989 | Hoeffkes et al. | 510/126 |
| 4,948,528 A | 8/1990 | Hoeffkes et al. | |
| 5,167,873 A | 12/1992 | Crutcher et al. | |
| 5,213,716 A | 5/1993 | Patel et al. | |
| 5,290,482 A | 3/1994 | Marschner et al. | |
| RE34,584 E | 4/1994 | Grote et al. | |
| 5,409,640 A | 4/1995 | Giret et al. | |
| 5,560,873 A | 10/1996 | Chen et al. | |
| 5,711,899 A * | 1/1998 | Kawa et al. | 516/77 |
| 5,883,058 A | 3/1999 | Wells et al. | |
| 5,925,340 A * | 7/1999 | Valdes et al. | 424/70.19 |
| 5,925,604 A * | 7/1999 | Chen et al. | 510/125 |
| 6,765,024 B1 * | 7/2004 | Gray et al. | 516/67 |

FOREIGN PATENT DOCUMENTS

WO    WO 98/38973    *   9/1998

* cited by examiner

*Primary Examiner*—Daniel S. Metzmaier
(74) *Attorney, Agent, or Firm*—Olson & Hierl, Ltd.

(57) ABSTRACT

Phase stable, pumpable, liquid, high solids, aqueous monoalkanolamide surfactant emulsions are disclosed for use as cold mixable monoalkanolamide delivery systems for separately prepared aqueous formulations containing at least one principal surfactant. The monoalkanolamide surfactant emulsions comprise at least one monoalkanolamide characterized in its unemulsified form by having an amide content of at least about 85% and by being substantially solid and water insoluble at a temperature below about 30° C., and at least one monoalkanolamide emulsifying surfactant and, surprisingly, remain homogeneous, pourable, and pumpable at a total solids content of at least 20 weight percent at a temperature in the range of about zero ° C. to about 30° C.

29 Claims, No Drawings

ALKANOLAMIDE SURFACTANT EMULSIONS AND PROCESS THEREFOR

CROSS-REFERENCE TO RELATED APPLICATIONS

This application is a continuation of U.S. patent application Ser. No. 09/937,592 filed on Sep. 27, 2001, now U.S. Pat. No. 6,765,024, which is a 371 of PCT/US00/09927 filed on Apr. 14, 2000, which claims the benefit of U.S. Provisional Application Ser. No. 60/287,574 filed on Apr. 14, 1999, the disclosures of which are incorporated herein by reference.

TECHNICAL FIELD OF THE INVENTION

This invention relates to novel liquid aqueous monoalkanolamide delivery systems and more particularly to liquid monoalkanolamide surfactant emulsions and cold mix processes therefor.

BACKGROUND OF THE INVENTION

For many years, alkanolamides, and particularly diethanolamides derived from lauric, stearic or coconut oil fatty acids, have been commonly and primarily employed as cost-effective foam boosters, foam stabilizers, and viscosity builders in liquid surfactant formulations where good foam generation is needed and desired. For example, foaming properties are particularly desirable and important in personal care cleanser products, such as shampoos, body cleansers; bubble baths and the like, and light duty household cleanser products, such as liquid dish washing products, liquid hand soaps and the like.

Cocodiethanolamides, in particular, have, for many years, been important nonionic surfactants in the industry and are commonly referred to as cocamide DEA, the name assigned this material in the *International Cosmetic Ingredient Dictionary*, Sixth Edition, published by The Cosmetic, Toiletry, and Fragrance Association (1995) (hereafter "INCI Dictionary"), the disclosures of which are incorporated herein by reference. Such name assignments are conventionally referred to as INCI names and will be so used herein.

Cocamide DEA derivatives are commercially available in pourable, pumpable, liquid form at ambient room temperature (about 30° C.), which form is particularly desirable, easy to handle and, in trade parlance, cold-mixable, i.e., desirably mixed into liquid formulations at ambient room temperature without requiring heating. Cold mixing is industrially desirable as it avoids heating the compounded formulation, thereby avoiding deteriorating heat-sensitive ingredients when present, minimizing the possibility of heat-induced product instability, reducing loss of volatiles, including water, lowering energy costs and manufacturing costs and the like.

Recently, however, the diethanolamines, which are used to manufacture diethanolamide derivatives, became the subject of certain animal toxicity studies which were reported to the public in the popular press. The negative press and toxicity issues raised by the publication of this report, in turn, created, in the minds of the public, a perceived toxicity associated with the presence of diethanolamides and of cocamide DEA, in particular, which appeared commonly as a listed ingredient on the labels of most personal care cleanser products. Consequently, this negative public opinion has created a need and desire in the personal care industry to replace diethanolamides with alternate foam boosters and foam stabilizers that are still functional, are substantially free of diethanonolamine or diethanolamides, and preferably are cold mixable at ambient room temperature.

It is known that monoalkanolamides, derived from the reaction of $C_2$—$C_6$ alkanolamines, such as monoethanolamine, isopropanolamine, diethylene glycolamine (2-(2-aminoethoxy)ethanol) and the like, and fatty acids having from about 8 to about 24 carbon atoms are potentially functional in applications requiring foam boosting, foam stabilizing and viscosity building. In particular, coconut oil derived monoethanolamine derivatives are of great commercial interest for use in personal care and household products.

Coconut monoethanolamide, referred to hereafter by the INCI name cocamide MEA, is known to have more foam boosting efficacy and more viscosity building efficacy than cocamide DEA. However, unlike cocamide DEA, cocamide MEA, is not commercially available as a pourable, pumpable, liquid form at ambient room temperature. The existing cocamide MEA products of commerce are normally substantially solid products sold in flaked form. Moreover, cocamide MEA is insoluble in water, so to incorporate it into an aqueous surfactant formulation, the compounded formulation must be heated above the melting point of cocamide MEA (above 60° C.). Additionally, cocamide MEA in heated molten form, as well as in unheated flaked form, is susceptible to browning discoloration on exposure to air during storage over a period of time. Such solubility and discoloration problems have limited the use of cocamide MEA, particularly in personal care products.

Monoalkanolamide derivatives prepared from the reaction of either monoethanolamine or isopropanolamine and vegetable oil unsaturated fatty acids, such as from soybean or canola (genetically modified rapeseed oil), have a lower melting point than that of coconut oil fatty acid derivatives, but also are not obtained in liquid form at ambient room temperature. These vegetable oil derived monoalkanolamides can be converted to a form remaining liquid at ambient room temperature with further chemical modification, such as alkoxylation with ethylene oxide, propoxylation with propylene oxide or a combination thereof. However, while such chemical modification can reduce the cloud point of the original starting monoalkanolamide, it normally produces an undesirable discolored product that is less effective than the unmodified monoalkanolamide in foam stabilizing or viscosity building properties. Further, the use of ethylene oxide is often looked upon as a "non-natural" feedstock, particularly from an environmental and aesthetic viewpoint, and can introduce other potentially toxic impurities, such as dioxane. Additionally, extra chemical processing increases handling and manufacturing costs.

It is known that soybean monoalkanolamide and canola monoalkanolamide derivatives prepared with diethylene glycolamine are in liquid form at ambient room temperature. However, such soybean and canola oil derived diglycolamides have undesirable brown colorations, undesirable strong odors and when used for viscosity control applications, produce an undesirable "stringy" viscosity, making them aesthetically and functionally unsuitable for personal care products. Additionally, the browning coloration of these monoalkanolamides in an air atmosphere typically worsens in appearance over time to a much greater extent than that normally observed in cocamide MEA.

Prior attempts to incorporate monoalkanolamides in surfactant formulations without heating the surfactant formulations have been made by employing solvents, such as cosmetically acceptable alcohols, for example, ethanol, isopropanol, and the like, or polyols, such as propylene glycol, glycerin and the like, or employing a hydrotroping agent, such as sodium xylene sulfonate. However, the use of solvents, particularly volatile alcohols, raises environmental issues and increases handling and manufacturing costs.

Thus, there is an ongoing, unresolved, commercial need for a relatively concentrated, high solids form of liquid monoalkanolamide delivery system, particularly for monoethanolamine, that can be cold mixed into separately prepared aqueous surfactant containing formulations, and cleanser formulations in particular, which typically contain a principal surfactant for the purpose of detersiveness and foaming. The novel cold mixable, liquid monoalkanolamide surfactant emulsions of this invention provide such a delivery system.

SUMMARY OF THE INVENTION

It has been discovered that pourable, pumpable, liquid aqueous monoalkanolamide surfactant emulsions can be prepared which are useful cold mixable delivery systems for incorporating monoalkanolamide into separately prepared aqueous formulations containing at least one surfactant.

The inventive liquid aqueous monoalkanolamide delivery system is in the form of a phase stable, pumpable, high solids monoalkanolamide surfactant emulsion at a temperature in the range of zero° C. to about 30° C. The monoalkanolamide surfactant emulsion preferably comprises, on a total emulsion weight basis:

about 1 to about 30 weight percent on an active weight basis of at least one monoalkanolamide characterized in it unemulsified form by having an amide content of at least 85%, and being substantially solid and water insoluble at a temperature below about 30° C.;

about 5 to about 30 weight percent on an active weight basis of at least one monoalkanolamide emulsifying surfactant;

zero to about 10 weight percent water soluble inorganic electrolyte salt;

zero to about 15 weight percent non-surfactant, organic solvent; and the balance being water. The monoalkanolamide surfactant emulsion contains a total solids content in the range of at least about 20 weight percent to not more than about 60 weight percent and is cold mixable into a separately prepared liquid aqueous formulation containing at least one principal surfactant.

Preferred monoalkanolamide surfactant emulsion embodiments have a weight ratio, on a active weight basis, of monoalkanolamide:emulsifying surfactant in the range of from about 1:6 to about 6:1. The monoalkanolamide emulsifying surfactants are preferably water soluble surfactants or salts thereof selected from the group consisting of amphoteric surfactants, zwitterionic surfactants, anionic surfactants, nonionic surfactants, cationic surfactants, and non-interactive mixtures thereof.

It was surprisingly found that liquid, aqueous monoethanolamide surfactant emulsion embodiments containing commercial cocamide MEA (having an amide content greater than 85%) remained homogeneous, pourable, pumpable and cold mixable at cocamide MEA active weight concentrations of about 5 to about 30 weight percent on a total emulsion weight basis.

Advantageously, the monoalkanolamide surfactant emulsions can be cold mixed into a formulation having at least one principal surfactant and provide foam boosting, foam stabilization, viscosity control or combination thereof. Further, the emulsifying agent employed can also have the dual function of being a secondary surfactant.

The monoalkanolamide surfactant emulsions beneficially provide a cost effective, cold mixable, liquid delivery system for incorporating monoalkanolamide MEA into personal care and household care cleansers. In particular, preferred cold mixable cocamide MEA surfactant emulsions beneficially retain the efficacy of cocamide MEA for foam boosting, foam stabilizing and viscosity control normally associated therewith and avoid the limitations of prior heat mixing processes.

DESCRIPTION OF THE PREFERRED EMBODIMENT

The term "monoalkanolamide" as used herein refers to monoalkanolamides which are the reaction products of $C_2$–$C_6$ alkanolamines having a primary amine functionality, such as monoethanolamine, isopropanolamine, diethylene glycolamine (2-(2-aminoethoxy)ethanol), and the like, and fatty acids having from about 8 to about 24 carbon atoms, preferably from about 10 to about 22 carbon atoms, more preferably from about 12 to about 18 carbon atoms, have an amide content of at least 85%, are normally substantially solid, and water insoluble at an ambient temperature of below about 30° C. The term "fatty acids" as used herein includes straight or branched chain, saturated or unsaturated fatty acids which are derived from fats, e.g., plant oils, tallow, and the like or synthesized, so long as the monoalkanolamine condensate thereof forms a monoalkanolamide surfactant emulsion.

The terms "cold mixable" and "cold mix" are used herein to refer to a mixing process, as by pumping, carried out at temperatures in the range of from zero° C. to about 30° C. The term "substantially solid" as used herein means that the compound or product is in a non-pourable paste or flake form, and is thereby non-liquid and non-pumpable for cold mix processing by conventional pumping equipment known in the processing arts.

The term "monoalkanolamide surfactant emulsion" as used herein refers to a homogeneous, high solids, pourable, pumpable, cold mixable liquid monoalkanolamide delivery system containing at least one monoalkanolamide and at least one monoalkanolamide emulsifying surfactant. The terms "homogeneous" and "phase stable" as applied to monoalkanolamide surfactant emulsions mean that no visible, physical phase separation of the monoalkanolamide from the aqueous medium is observed on storage standing at an ambient temperature in the range of about zero° C. to about 30° C., over a period of at least one week. The term "high solids" as used herein means that the sum of all non-volatile components in the emulsion is in the range of at least about 20 weight percent to not more than about 60 weight percent, preferably in the range of about 25 weight percent to not more than about 55 weight percent, of the total emulsion weight.

Monoalkanolamides useful herein can be made by any process known in the art so long as they form a monoalkanolamide surfactant emulsion. Commercially available monoalkanolamides suitable for preparing monoalkanolamide surfactant emulsions of this invention are available from a number of suppliers and can be prepared by any of various known synthetic processes, such as, but not limited to, the catalytic trans-esterification of fatty acids or derivatives thereof (commonly referred to as superamides) or by direct amidation of fatty acids with $C_2$–$C_6$ alkanolamine. Non-limiting examples of commercially available monoalkanolamides and suppliers are found in the INCI Dictionary, incorporated herein by reference.

Preferred monoalkanolamides are alkanolamine condensates of fatty acids such as, but not limited to, lauric acid, palmitic acid, stearic acid, oleic acid, linoleic acid and fatty acids derived from plant oils such as, but not limited to coconut oil, soybean oil, canola oil (genetically modified Canadian rapeseed oil), wheat germ oil, peanut oil, corn oil, olive oil, and the like and mixtures thereof. As long as a monoalkanolamide surfactant emulsion can be formed, the type of plant oil employed for making monoalkanolamide derivatives is limited only by economics or commercial production of such oils.

Preferred monoalkanolamides are monoethanolamides, such as, but not limited to, coconut monoethanolamide (cocamide MEA), lauric monoethanolamide, stearic monoethanolamide, oleic monoethanolamide, and linoleic monoethanolamide. Cocamide MEA is particularly preferred. A preferred monoisopropanolamide is lauric isopropanolamide, and a preferred diethylene glycolamide is coconut diglycolamide.

The monoalkanolamide surfactant emulsions can be prepared by emulsifying at least one monoalkanolamide with a sufficient amount of at least one monoalkanolamide emulsifying surfactant in an aqueous emulsifying medium by heating the emulsifying medium to a temperature below about 90° C., preferably in the range of about 40° to about 70° C., for a period sufficient to substantially solubilize the monoalkanolamide to a homogeneous emulsion, and then cooling the monoalkanolamide surfactant emulsion. Surprisingly, the so formed, high solids, monoalkanolamide surfactant emulsion on cooling remains in a homogeneous, pourable, and pumpable liquid form at a temperature in the range of from about zero° C. to about 30° C.

A preferred monoalkanolamide surfactant emulsion can be formed by first emulsifying the monoalkanolamide at a temperature in the range of about 40° to about 70° C. with the emulsifying surfactant in the form of an aqueous concentrate containing at least about 30 weight percent water, and second adjusting the total solids content of the so formed emulsion at a temperature preferably in the range of about 40° to about 50° C. by adding sufficient water thereto. More preferably, the foregoing monoalkanolamide surfactant emulsion is formed under an inert atmosphere, preferably nitrogen, to minimize browning discoloration of the monoalkanolamide.

The monoalkanolamide surfactant emulsions can be prepared and stored for future use or alternatively, be prepared for substantially immediate use as a liquid monoalkanolamide delivery system in cold mix processes.

The type and amount of monoalkanolamide and emulsifying surfactant employed for preparing the inventive surfactant emulsions is limited only to the extent to which the emulsifying surfactant is capable of emulsifying the monoalkanolamide and producing a monoalkanolamide surfactant emulsion. Preferably, a monoalkanolamide surfactant emulsion contains, on a total emulsion weight basis, about 1 to about 30 weight percent of an active weight basis of a monoalkanolamide is emulsified with about 5 to about 30 weight percent on an active weight basis of monoalkanolamide emulsifying surfactant.

Preferably the weight ratio of monoalkanolamide:emulsifying surfactant employed on an active weight basis is in the range of about 1:6 to about 6:1, more preferably in the range of from about 1:5 to about 5:1, most preferably in the range of from about 1:4 to about 4:1. The term "active weight" is used herein to denote the concentration of "active" monoalkanolamide or emulsifying surfactant in the monoalkanolamide surfactant emulsion.

The emulsifying surfactants preferably, without being limited thereto, are water soluble surfactants or salts thereof selected from the group consisting of amphoteric surfactants, zwitterionic surfactants, anionic surfactants, nonionic surfactants, cationic surfactants and non-interactive mixtures thereof. It is recognized that interaction between certain cationic surfactants and anionic surfactants may occur which precipitate as water-insoluble solids, but it is also recognized that compatible mixtures of cationically charged surfactants and anionic surfactants are known in the art. Thus, the type of emulsifying surfactant and surfactant mixture employed is not limited so long as interaction, if any, between surfactants does not result in solid precipitate formation and interfere with the formation of the monoalkanolamide surfactant emulsion.

The term "amphoteric surfactants" refers to that class of surfactants that can exist in three different charged forms depending on pH; i.e., cationic, zwitterionic or anionic, and includes the water-soluble salts thereof. Suitable amphoteric surfactants include, but are not limited to, acylamphoacetate, acylamphodiacetates, acylamphopropionates, wherein the acyl group has from about 8 to about 22 carbon atoms. Preferred amphoteric surfactants include, but are not limited to, sodium cocoamphoacetate, sodium lauroamphoacetate, disodium caprylamphoacetate, disodium cocoamphodiacetate, disodium lauroamphodiacetate, disodium wheat germamphodiacetate, sodium cocoamphopropionate, disodium capryloamphodipropionate, disodium cocoamphodipropionate, disodium lauroamphodipropionate and the like. Sodium cocoamphopropionate is particularly preferred.

The term "zwitterionic surfactant" refers to that class of surfactants that can exist as intronium or inner salts (i.e., in zwitterionic form) at a pH at and above their isoelectric points (neutral and alkaline pH) and are either zwitterionic or cationic below their isoelectric points (acid pH). Suitable zwitterionic surfactants include, but are not limited to, betaine surfactants, such as alkyl betaine, alkylamido betaine and the like and sulfobetaines (sultaines), such as alkyl sultaine, alkylamido sultaine and the like, wherein the alkyl group from about 8 to about 22 carbon atoms. Particularly preferred are betaines including, but not limited to, cocobetaine (cocodimethylglycine), octyl betaine, lauryl betaine cetyl betaine, oleyl betaine, cocoamidopropyl betaine, laurylamido betaine, oleylamidopropyl betaine, isostearamidopropyl betaine, and wheat germamidopropyl betaine.

Anionic surfactants preferably include, without being limited thereto, alkyl sulfates, alkylether sulfates having from 1 to about 10 moles ethylene oxide groups, acylisethionates, sarcosinates, sulfosuccinates and alkali metal salts thereof, wherein the alkyl group or acyl group has from about 8 to about 24 carbon atoms, preferably from about 12 to about 18 carbon atoms, and mixtures thereof. Sodium salts of alkylether sulfates having an average range of from 1 to 4 moles, preferably 3 moles, ethylene oxide are particularly preferred.

Nonionic surfactants preferably include, without being limited thereto, polyethylene oxide condensates of alkyl phenols having an alkyl group, polyoxyethylene alkyl ethers and polyethylene glycol glyceryl fatty esters and the like wherein the alkyl group has from about 6 to about 22 carbon atoms and the polyethylene or polyoxyalkylene groups are derived from about 1 to about 200 moles, preferably from about 10 to about 100 moles, of ethylene oxide, propylene oxide, mixed ethylene oxide and propylene oxide and mixtures thereof.

Cationic surfactants preferably include, without being limited thereto, cetyltrimethyl ammonium chloride, oleyldimethylbenzyl ammonium chloride, stearyldimethylbenzyl ammonium chloride and the like and alkyl amine oxides having from about 8 to 18 carbon atoms in the alkyl group that are cationically charged in acid media.

Commercially available emulsifying surfactants useful for preparing the monoalkanolamide surfactant emulsions are available from a number of suppliers, and a non-limiting list of emulsifying surfactants can be found in the INCI Dictionary. Preferably the emulsifying surfactants are in the form of aqueous concentrates containing at least about 30 weight percent water.

The selection of the emulsifying surfactant may, but need not, be determined by the class and purpose of the principal surfactant in the aqueous formulation into which the monoalkanolamide surfactant emulsion is subsequently cold mixed or the purpose of the finished product. Thus, the emulsifying surfactant, for example, can be a secondary surfactant, or cosurfactant for the principal surfactant in the final formulation.

As used herein, the term "principal surfactant" refers to the main active, detersive or foaming surfactant employed in an aqueous formulation, such as a liquid cleanser or the like for the purpose of providing cleansing, and the term "secondary surfactant" refers to milder, lower foaming surfactants that are commonly employed for added skin protective effects, such as conditioning, or product stabilizing effects, such as viscosity control, lime soap dispersing, and the like. Therefore, it is recognized that the emulsifying surfactants may be in the same or different class as the principal surfactant in the final formulation into which the monoalkanolamide surfactant emulsion is subsequently cold mixed.

Monoalkanolamide surfactant emulsions can be subsequently cold mixed into separately prepared aqueous formulations containing at least one principal surfactant at a temperature of below about 30° C. to provide finished products having foam and viscosity characteristics at parity with or greater than that normally achieved with conventional diethanolamides.

The novel monoalkanolamide surfactant emulsions can range from substantially transparent microemulsions to substantially opaque, white, pearlescent macroemulsions. Substantially transparent microemulsions preferably have a cloud point of not more than about 5° C. Surprisingly, substantially opaque, white pearlescent monoalkanolamide surfactant emulsions not only remained homogeneous, they substantially immediately dispersed, when subsequently incorporated by cold mixing process into a formulation containing at least one principal surfactant to produce a substantially clear final product. The amount of monoalkanolamide surfactant emulsion employed can be readily determined by those skilled in the formulation arts to achieve the desired foam boosting, foam stabilizing, and viscosity control desired. Typically amounts of from about 1 to about 5 active weight percent monoalkanolamide are employed in finished products.

Principal surfactants can be water soluble surfactants or salts thereof selected from the group consisting of anionic surfactants, nonionic surfactants, amphoteric surfactants, zwitterionic surfactants, cationic surfactants and non-interactive mixtures thereof and can be of the same or different surfactant class as the emulsifying surfactants.

Monoethanolamide surfactant emulsions, in particular, are useful as monoethanolamide delivery systems for aqueous cleanser formulations in which the principal surfactant is a detersive surfactant.

Principal detersive surfactants are conventionally employed in liquid personal care cleansers, such as shampoos, liquid soaps, bubble baths and the like, and for light duty liquid household cleansers, such as liquid dish washes, liquid hand soaps and the like, for the purpose of cleansing. Commonly such detersive surfactants are generally anionic surfactants and alkali metal salts thereof selected from the group consisting of, but not limited to, alkylaryl sulfonates, the so-called soft alkylates, alkyl sulfates, alkylether sulfates having 1 to about 10 moles ethylene oxide-groups, alkyl sulfonates, preferably alpha olefin sulfonates, sulfosuccinates, and the like, where the alkyl group contains from about 8 to about 22 carbon atoms. Particularly preferred are dodecylbenzenesulfonates, sodium lauryl sulfate; sodium lauryl ethersulfate, having an average of about 3 moles ethylene oxide, and sodium $C_{12}$—$C_{14}$ olefin sulfonates.

The aqueous monoalkanolanide emulsifying surfactant medium primarily constitutes water, preferably at least about 30 weight percent water on a total weight basis of the monoalkanolamide surfactant emulsion, but the exact amount of water will vary with the amount of water present in the emulsifying surfactant. It is also known and recognized that commercial monoalkanolamide and emulsifying surfactants may contain minor amounts, typically not more than about 15 weight percent on a total actives weight as supplied basis, of non-surfactant, organic solvents such as polyols, alcohols or not more than about 10 weight percent inorganic electrolytes remaining as reaction byproducts or impurities from the feedstock employed for manufacture. For example, typical byproducts of triglyceride containing reactants, such as coconut oils and other glyceride containing plant oils, can be glycerin, inorganic salts, such as alkali metal salts of hydrochloric or sulfuric acids, soaps and the like, which are substantially non-toxic to humans and cosmetically acceptable. Other non-surfactant components that may be present in relatively low amounts, typically not more than about 10 weight percent on a total active material weight as supplied basis, include cosmetically acceptable solvents, such as ethanol, and propylene glycol.

Water-soluble inorganic electrolytes, such as alkali metal salts of hydrochloric acid and sulfuric acid are optionally added to liquid surfactant formulations to control viscosity. Sodium chloride is particularly commonly used as a low cost electrolyte and the inventive monoalkanolamide surfactant emulsion provides the formulator the option of adding or not adding inorganic electrolyte. The monoalkanolamide surfactant emulsion may optionally contain, on a total emulsion weight basis, minor amounts, e.g. up to about 10 percent by weight of inorganic salt, preferably sodium chloride, present as byproducts in the commercial amide and emulsifying surfactant employed.

A particularly preferred monoethanolamide surfactant emulsion embodiment, having a total solids content in the range of at least about 30 weight percent to not more than about 55 weight percent, useful for cold mixing processes can be prepared by emulsifying monoethanolamide in an active amount, on a total emulsion weight basis, of about 6 to about 25 weight percent, with at least one zwitterionic or amphoteric emulsifying surfactant in an aqueous medium containing a weight ratio, on an active weight basis, of monoethanolamide:emulsifying surfactant of about 1:6 to about 6:1 at a temperature in the range of about 40° C. to about 70° C., preferably in the range of about 60° to about 70° C., so maintained until homogeneous and then cooled to ambient room temperature for storage.

Surprisingly, monoethanolamide surfactant emulsion embodiments containing commercial cocamide MEA (having an amide content greater than 85%) remained phase stable, homogeneous, pourable, pumpable and cold mixable at ambient temperatures in the range of about zero° C. to about 30° C., at a cocamide MEA active concentration, on a total emulsion weight basis, of about 6 to about 25 weight percent at a total solids content in the range of about 20 to not more than about 60 weight percent on a total emulsion weight basis.

Particularly preferred monoethanolamide surfactant emulsion embodiments contain, on a total emulsion weight basis, from about 6 weight percent to about 25 weight percent on an active weight basis of cocamide MEA; from about 5 weight percent to about 30 weight percent on an active weight percent basis of an amphoteric or zwitterionic emulsifying surfactant, preferably a betaine surfactant and the balance being water. Another such particularly preferred cocamide MEA surfactant emulsion embodiments can also include an anionic emulsifying surfactant and, on a total emulsion weight basis, from zero to about 10 weight percent sodium chloride, from zero to about 10 weight percent ethanol and optionally, fragrance.

The following examples further illustrate the preparation and use of the inventive monoethanolamide surfactant emulsions but are not intended as a limitation thereof. Unless otherwise specified, quantities mentioned in the examples are parts by weight of commercial material on an as supplied basis.

EXAMPLE 1

This example illustrates a monoalkanolamide surfactant emulsion embodiment containing a weight ratio of monoethanolamide:cocamidopropylbetaine emulsifying surfactant of about 1:4 to about 1:5 on an active weight basis. An aqueous surfactant medium was prepared by adding 6 parts by weight of coconut monoethanolamide (MACKAMIDE™ CMA, at least 85% amide content, McIntyre Group Ltd.) to 94 parts by weight of aqueous 35% cocamidopropyl betaine (MACKAM™ 35, about 5% sodium chloride, McIntyre Group Ltd.). The aqueous surfactant medium was then heated with mixing agitation to a temperature in the range of from about 60° to about 70° C., so maintained until substantially clear and homogeneous and then cooled to an ambient room temperature of about or below 30° C. The cooled monoethanolamide surfactant emulsion was a pourable, substantially transparent, liquid microemulsion, with a viscosity of less than about 5,000 centipoises (cps) at a temperature of about 25° C., (spindle no. 3, 12 rpm, Brookfield LVT viscometer), and was pumpable at an ambient temperature below 30° C.

A liquid microemulsion can have a total solids content in the range of least about 35 to about 45 weight percent of the total microemulsion weight and preferably has a cloud point in the range of about 5° C. and −20° C.

Alternatively, the foregoing emulsion was prepared by heating the aqueous cocamidopropylbetaine to a temperature in the range of about 65° to about 70° C., maintaining the foregoing temperature while slowly adding the coconut monoethanolamide under stirring agitation until the coconut monoethanolamide was solubilized and the emulsion was homogeneous, the total solids were then adjusted and the microemulsion further cooled to a temperature in the range of about 35° to about 45° C., for storage packaging.

In another embodiment, freshly synthesized coconut monoethanolamide, while still in molten form, can be employed for preparing the foregoing microemulsion.

EXAMPLE 2

This example illustrates a monoalkanolamide surfactant emulsion embodiment containing a weight ratio of monoethanolamide:cocamidopropylbetaine emulsifying surfactant of about 1:1 on an active weight basis. An aqueous surfactant medium was prepared containing 12 parts by weight coconut monoethanolamide (MACKAMIDE™ CMA, McIntyre Group Ltd.), 12 parts by weight of cocamidopropyl betaine added as 34.3 parts by weight of aqueous 35% cocamidopropyl betaine (MACKAM™ 35, McIntyre Group Ltd.) and 53.7 parts by weight deionized water and then heated with mixing agitation to a temperature in the range of about 60° to about 70° C., so maintained until substantially clear and homogeneous and then cooled to an ambient room temperature of below about 30° C. The cooled monoethanolamide surfactant emulsion was a pourable, white, pearlescent liquid emulsion that remained physically stable (no phase separation) and was readily pumpable at an ambient temperature below 30° C.

EXAMPLE 3

This example illustrates a monoalkanolamide surfactant emulsion embodiment containing a weight ratio of monoethanolamide:cocobetaine emulsifying surfactant of about 1:1 on an active weight basis. An aqueous surfactant medium was prepared by combining 25 parts by weight coconut monoethanolamide (MACKAMIDE™ CMA, McIntyre Group Ltd.), 75 parts by weight of aqueous 35% cocobetaine (MACKAM™ CB-35, about 6% sodium chloride, McIntyre Group Ltd.) and 50 parts by weight deionized water. The surfactant medium was then heated with mixing agitation to a temperature in the range of from about 60° to about 70° C., so maintained until substantially clear and homogeneous and then cooled to an ambient room temperature of below about 30° C. The cooled monoethanolamide surfactant emulsion was a pourable, white pearlescent liquid emulsion that remained physically stable (no phase separation) and was readily pumpable at an ambient temperature below 30° C.

Alternatively, the foregoing emulsion was prepared by heating the aqueous cocobetaine under a nitrogen atmosphere to a temperature in the range of about 60° to about 70° C., maintaining the foregoing temperature while slowly adding the coconut monoethanolamide under stirring agitation until the coconut monoethanolamide was solubilized and the emulsion was homogeneous, the emulsion was then cooled to a temperature in the range of about 40° to about 50° C., the total solids were adjusted to a range of about 48 to about 51 weight percent of the total emulsion weight and the adjusted emulsion further cooled to an ambient room temperature in the range of about 30° to about 40° C.

EXAMPLE 4

This example illustrates a monoalkanolamide surfactant emulsion containing a weight ratio of monoethanolamide: sodium cocoamphopropionate emulsifying surfactant of about 1.6:1 on an active weight basis. An aqueous surfactant medium was prepared by combining 25 parts by weight coconut monoethanolamide (MACKAMIDE™ CMA, McIntyre Group Ltd.), 37 parts by weight of aqueous 40% sodium cocoamphopropionate (MACKAM™ CSF-CG, McIntyre Group Ltd.) and 38 parts by weight water and then heated with stirring agitation to a temperature in the range of from about 60° to about 70° C., so maintained until substantially clear and homogeneous and then cooled to an ambient room temperature of below about 30° C. The cooled monethanolamide surfactant emulsion was a pourable, white pearlescent liquid emulsion, that remained physically stable (no phase separation) and was readily pumpable at an ambient temperature below 30° C.

EXAMPLE 5

This example illustrates a monoalkanolamide surfactant emulsion prepared with a binary mixture of surfactant emulsifying agents, containing a weight ratio of monoethanolamide:sodium cocoamphopropionate:sodium laureth sulfate emulsifying surfactants of about 1:0.4:1 on an active weight basis. An aqueous surfactant medium was prepared by combining 25 parts by weight coconut monoethanolamide (MACKAMIDE™ CMA, McIntyre Group Ltd.), 25 parts by weight of aqueous 40% sodium cocoamphopropionate (MACKAM™ CSF-CG, McIntyre Group Ltd.), 40 parts by weight of aqueous 60% sodium laureth-3 sulfate (average of about 3 moles ethylene oxide) and 10 parts by weight deionized water. The surfactant medium was then heated with mixing agitation to a temperature in the range of from about 60° to about 70° C., so maintained until substantially clear and homogeneous and then cooled to an ambient room temperature of below about 30° C. The cooled monethanolamide surfactant emulsion was a pourable, white, pearlescent liquid emulsion that remained physically stable (no phase separation) and was readily pumpable at a temperature below 30° C.

EXAMPLE 6

This example illustrates a monoalkanolamide surfactant emulsion containing a weight ratio of lauric isopropanolamide:lauryl betaine emulsifying surfactant of about 1:1 on an active weight basis. An aqueous surfactant medium was prepared by combining 20 parts by weight lauric isopropanolamide, 70 parts by weight of aqueous 35% lauryl betaine and 10 parts by weight deionized water. The surfactant medium was then heated with mixing agitation to a temperature in the range of from about 60° to about 70° C., so maintained until substantially clear and homogeneous and then cooled to an ambient room temperature of below about 30° C. The cooled isopropanolamide surfactant emulsion was a pearlescent liquid emulsion that remained physically stable (no phase separation) and was readily pourable and pumpable at a temperature below 30° C.

EXAMPLE 7

This example illustrates a monoalkanolamide surfactant emulsion containing a weight ratio of coconut diglycolamide:cocamidopropyl betaine emulsifying surfactant of about 1:1 on an active weight basis. An aqueous surfactant medium was prepared by combining 20 parts by weight coconut diglycolamide, 70 parts by weight of aqueous 35% cocamidopropyl betaine and 10 parts by weight water. The surfactant medium was then heated with mixing agitation to a temperature in the range of from about 40° to about 60° C., so maintained until substantially clear and homogeneous and then cooled to an ambient room temperature of below about 30° C. The cooled diglycolamide surfactant emulsion was a pearlescent liquid emulsion that remained physically stable (no phase separation) and was readily pourable and pumpable at an ambient temperature below 30° C.

EXAMPLE 8

This example illustrates the effective use of the inventive monoalkanolamide surfactant emulsions as improved delivery systems in cold mixing processes.

A clear, light duty, liquid cleanser containing anionic surfactant as the principal surfactant was prepared in a cold mixing process with all ingredients at an ambient temperature of below 30° C. as follows. First, an aqueous solution of 80 parts by weight of aqueous 15% sodium lauryl sulfate was placed under mixing agitation and then 20 parts by weight of a pearlescent monoethanolamide surfactant emulsion previously prepared as described in example 2 was cold mixed therein. The pearlescent surfactant emulsion substantially immediately dissolved into the anionic surfactant solution and a clear, light duty, liquid cleanser was obtained within about 4 minutes without requiring any heating.

EXAMPLE 9

This comparative example illustrates the need to use conventional heat processing methods when the inventive monoalkanolamide surfactant emulsions are not employed.

A mixture of 80 parts of an aqueous 15% sodium lauryl sulfate solution, and 18.6 parts by weight of aqueous 35% cocamidopropyl betaine was prepared at an ambient room temperature of below about 30° C. and then 1.4 parts by weight of coconut monoethanolamide in solid, flaked form was added with mixing agitation. After a mixing period of about 5 hours at ambient room temperature, the solid flaked coconut monoethanolamide was still in suspension and undissolved.

The same mixture was then heated to above the melting point of the coconut monoethanolamide; i.e., to above about 60° C., at which temperature the coconut monoethanolamide solubilized and formed a clear product which remained clear on cooling to ambient room temperature.

EXAMPLE 10

This example illustrates the effective use of the inventive monoalkanolamide surfactant emulsions as fragrance solubilizers in cold mixing processes.

A fragranced monoethanolamide surfactant emulsion was prepared by cold mixing equal parts by weight of lemon fragrance and a monoethanolamide surfactant emulsion of Example 3 to disperse the fragrance. The fragranced monoethanolamide surfactant emulsion was a pourable, pearlescent liquid.

The fragranced monoethanolamide surfactant emulsion, 20 parts by weight, was then subsequently cold mixed (at a temperature of below 30° C.) into 80 parts by weight of an aqueous 15% sodium laureth-3 sulfate solution with mixing agitation. The pearlescent fragranced monoethanolamide surfactant emulsion substantially immediately dissolved into the anionic surfactant solution and a substantially clear, fragranced, liquid cleanser was obtained within several minutes.

The present invention has been described generally and with respect to preferred embodiments. It will be understood that modifications and variation of the disclosed composition and processes may be made without departing from the spirit and scope of the novel concept of the present invention.

We claim:

1. A liquid monoalkanolamide surfactant emulsion useful as an aqueous monoalkanolamide delivery system in a cold mixing process, the liquid monoalkanolamide surfactant emulsion consisting of:
   (a) a monoalkanolamide, which in unemulsified form is substantially solid and water insoluble at a temperature below about 30° C.;
   (b) a monoalkanolamide emulsifying effective amount of an amphoteric emulsifying surfactant; and on a total monoalkanolamide surfactant emulsion basis,
   (c) a water soluble inorganic electrolyte salt present in an amount of not more than about 10 weight percent;
   (d) a non-surfactant organic solvent present in an amount of not more than about 15 weight percent;
   (e) an optional fragrance; and
   (f) the balance being a sufficient amount of water to obtain a total solids content in the range of about 20 to about 60 weight percent;
   wherein the liquid monoalkanolamide surfactant emulsion is cold mixable into a separately prepared liquid aqueous formulation containing at least one principal surfactant to form a finished product, and is phase stable and pumpable at a temperature in the range of about zero to about 30° C.

2. The liquid monoalkanolamide surfactant emulsion of claim 1 wherein the monoalkanolamide is present in an amount in the range of about 1 to about 30 weight percent on a total monoalkanolamide surfactant emulsion weight basis.

3. The liquid monoalkanolamide surfactant emulsion of claim 1 wherein the monoalkanolamide emulsifying surfactant is present in an amount in the range of about 5 to about 30 weight percent on a total monoalkanolamide surfactant emulsion weight basis.

4. The liquid monoalkanolamide surfactant emulsion of claim 1 wherein the monoalkanolamide is selected from the group consisting of a monoethanolamide, a monoisopropanolamide, a diethylene glycolamide, and mixtures thereof.

5. The liquid monoalkanolamide surfactant emulsion of claim 1 wherin the monoalkanolamide is a monoethanolamide, which is present in an amount in the range of about 6 to about 25 weight percent by weight on a total monoalkanolamide surfactant emulsion weight basis.

6. The monoalkanolamide surfactant emulsion of claim 1 wherein the monoalkanolamide includes an acyl group having about 8 to about 24 carbon atoms.

7. The monoalkanolamide surfactant emulsion of claim 1 wherein the monoalkanolamide is selected from the group consisting of an alkanolamine condensate of a fatty acid selected from the group consisting of lauric acid, palmitic acid, stearic acid, oleic acid, linoleic acid, and a mixture thereof.

8. The monoalkanolamide surfactant emulsion of claim 1 wherein the monoalkanolamide is an alkanolamine condensate of a fatty acid derived from a plant oil.

9. The monoalkanolamide surfactant emulsion of claim 1 wherein the monoalkanolamide is selected from the group consisting of coconut monoethanolamide, laurie monoethanolamide, stearic monoethanolamide, oleic monoethanolamide, linoleic monoethanolamide, lauric. isopropanolamide, coconut diglycolamide, and a mixture thereof.

10. The monoalkanolamide surfactant emulsion of claim 1 wherein the amphoteric monoalkanolamide emulsifying surfactant is selected from the group consisting of an acylamphoacetate, an acylamphodiacetate, an acylamphopropionate, an acylamphodipropionate, and a mixture thereof, wherein the acyl group of the amphoteric surfactant has about 8 to about 22 carbon atoms.

11. The monoalkanolaniide surfactant emulsion of claim 1 wherein the inorganic electrolyte salt is selected from the group consisting of an alkali metal salt of hydrochloric acid, an alkali metal salt of sulfuric acid, and a mixture thereof.

12. The monoalkanolarnide surfactant emulsion of claim 1 wherein the non-surfactant organic solvent is a cosmetically acceptable polyol, alcohol, or a mixture thereof.

13. The monoalkanolamide surfactant emulsion of claim 1 wherein the monoalkanolamide is coconut monoethanolamide.

14. A liquid monoethanolamide surfactant emulsion useful as an aqueous monoethanolamide delivery system in a cold mixing process, the liquid monoethanolamide surfactant emulsion consisting of:
   (a) about 6 to about 25% by weight of a monoethanolamide on a total monoethanolamide surfactant emulsion weight basis, wherein the monethanolamide, in unemulsified form is substantially solid and water insoluble at a temperature below about 30° C.;
   (b) about 5 to about 30% by weight of monoalkanolamide emulsifying effective amount of a zwitterionic emulsifying surfactant; and on a total monoethanolamide surfactant emulsion weight basis,
   (c) a water soluble inorganic electrolyte salt present in an amount of not more than about 10 weight percent;
   (d) a non-surfactant organic solvent present in an amount of not more than about 15 weight percent;
   (e) an optional fragrance; and
   (f) the balance being a sufficient amount of water to obtain a total solids content in the range of about 20 to about 60 weight percent;
   wherein the liquid monoethanolamide surfactant emulsion is cold mixable into a separately prepared liquid aqueous formulation containing at least one principal surfactant to form a finished product, and is phase stable and pumpable at a temperature in the range of about zero to about 30° C.

15. The monoethanolamide surfactant emulsion of claim 14 wherein the monoalkanolamide emulsifying surfactant is a zwitterionic surfactant selected from the group consisting of an alkyl betaine, an alkylamido betaine, an alkyl sulfobetaine, an alkylamido sulfobetaine, and a mixture thereof, wherein the alkyl group of the zwitterionic surfactant has about 8 to about 22 carbon atoms.

16. The monoethanolamide surfactant emulsion of claim 14 wherein the monoalkanolamide emulsifying surfactant is cocobetaine.

17. The monoethanolamide surfactant emulsion of claim 14 wherein the monoalkanolamide emulsifying suifactant is cocamidopropyl betaine.

18. The monoethanolamide surfactant emulsion of claim 14 wherein the monoalkanolamide emulsifying surfactant is lauryl betaine.

19. The monoethanolamide surfactant emulsion of claim 14 wherein the monoethanolamide includes an acyl group having about 8 to about 24 carbon atoms.

20. The monoethanolamide surfactant emulsion of claim 14 wherein the monoethanolamide is an ethanolamine condensate of a fatty acid selected from the group consisting of lauric acid, palmitic acid, stearic acid, oleic acid, linoleic acid, and a mixture thereof.

21. The monoethanolamide surfactant emulsion of claim 14 wherein the monoethanolamide is an ethanolamine condensate of a fatty acid derived from a plant oil.

22. The monoethanolamide surfactant emulsion of claim 14 wherein the monoethanolamide is selected from the group consisting of coconut monoethanolamide, lauric monoethanolamide, stearic monoethanolamide, oleic monoethanolamide, linoleic monoethanolamide, and a mixture thereof.

23. A liquid monoethanolamide surfactant emulsion useful as an aqueous monoethanolamide delivery system in a cold mixing process, the liquid monoethanolamide surfactant emulsion consisting of:
  (a) about 6 to about 25% by weight of a monoethanolamide on a total monoethanolamide surfactant emulsion weight basis, wherein the monethanolamide, in unemulsified form is substantially solid and water insoluble at a temperature below about 30° C.;
  (b) about 5 to about 30% by weight of a monoalkanolaniide emulsifying effective amount of an amphoteric emulsifying surfactant; and on a total monoethanolamide surfactant emulsion weight basis,
  (c) a water soluble inorganic electrolyte salt present in an amount of not more than about 10 weight percent;
  (d) a non-suifactant organic solvent present in an amount of not more than about 15 weight percent;
  (e) an optional fragrance; and
  (f) the balance being a sufficient amount of water to obtain a total solids content in the range of about 20 to about 60 weight percent;
  wherein the liquid monoethanolamide surfactant emulsion is cold mixable into a separately prepared liquid aqueous formulation containing at least one principal surfactant to form a finished product, and is phase stable and pumpable at a temperature in the range of about zero to about 30° C.

24. The monoethanolamide surfactant emulsion of claim 23 wherein the monoalkanolamide emulsifying surfactant is an amphoteric surfactant selected from the group consisting of an acylamphoacetate, an acylamphodiacetate, an acylamphopropionate, an acylamphodipropionate, and a mixture thereof, wherein the acyl group of the amphoteric surfactant has about 8 to about 22 carbon atoms.

25. The monoethanolamide surfactant emulsion of claim 23 wherein the monoalkanolamide emulsifying surfactant is sodium cocoamphopropionate.

26. The monoethanolamide surfactant emulsion of claim 23 wherein the monoethanolamide includes an acyl group having about 8 to about 24 carbon atoms.

27. The monoethanolamide surfactant emulsion of claim 23 wherein the monoethanolamide is an ethanolamine condensate of a fatty acid selected from the group consisting of lauric acid, palmitic acid, stearic acid, oleic acid, linoleic acid, and a mixture thereof.

28. The monoethanolamide surfactant emulsion of claim 23 wherein the monoethanolamide is an ethanolamine condensate of a fatty acid derived from a plant oil.

29. The monoethanolamide surfactant emulsion of claim 23 wherein the monoethanolamide is selected from the group consisting of coconut monoethanolamide, lauric monoethanolamide, stearic monoethanolamide, oleic monoethanolamide, linoleic monoethanolamide, and a mixture thereof.

* * * * *

UNITED STATES PATENT AND TRADEMARK OFFICE
CERTIFICATE OF CORRECTION

PATENT NO. : 7,282,524 B2
APPLICATION NO. : 10/892750
DATED : October 16, 2007
INVENTOR(S) : John Gray and Eugene D'Aversa It is certified that error appears in the above-identified patent and that said Letters Patent is hereby corrected as shown below:

Col. 13, line 14, Claim 1, change "emulsion basis" to read --emulsion weight basis--.

Col. 13, line 53, Claim 7, change "alkanolamme" to read --alkanolamine--.

Col. 13, line 62, Claim 9, change "laurie" to read --lauric--; Col. 13, line 64, change "lauric." to read --lauric--.

Col. 14, line 25, Claim 14, insert --a-- before "monoalkanolamide"

Col. 14, line 55, Claim 17, change "suifactant" to read --surfactant--.

Col. 15, lines 19-20, Claim 23, change "monoalkanola-niide" to read --monoalkanolamide--; Col. 15, line 25, change "non-suifactant" to read --non-surfactant--.

Signed and Sealed this

Tenth Day of June, 2008

JON W. DUDAS
*Director of the United States Patent and Trademark Office*